United States Patent [19]

Nakamatsu et al.

[11] Patent Number: 5,276,198
[45] Date of Patent: Jan. 4, 1994

[54] PROCESS FOR PRODUCING 2-METHYL-1,3-CYCLOHEXANEDIONE AND 2-METHYLRESORCINOL

[75] Inventors: Toshio Nakamatsu, Kobe; Yasuhiro Nishida, Itami; Norio Kometani, Kishiwada, all of Japan

[73] Assignees: Sumitomo Chemical Company, Limited; Sumika Fine Chemicals Co., Ltd., both of Osaka, Japan

[21] Appl. No.: 933,175

[22] Filed: Aug. 21, 1992

[30] Foreign Application Priority Data

Aug. 30, 1991 [JP] Japan .................................. 3-219802

[51] Int. Cl.$^5$ ............................................ C07C 45/65
[52] U.S. Cl. .................................. 568/350; 564/446; 568/772
[58] Field of Search ................. 564/446; 568/350, 351, 568/772

[56] References Cited

U.S. PATENT DOCUMENTS

| | | | |
|---|---|---|---|
| 3,100,205 | 8/1963 | Schulte et al. | 564/455 |
| 3,969,409 | 7/1976 | Miyano et al. | 564/455 |
| 4,160,113 | 7/1979 | Müller et al. | 568/772 |
| 4,212,823 | 7/1980 | Muller | 564/446 |
| 4,250,336 | 2/1981 | Muller et al. | 568/772 |
| 4,431,848 | 2/1984 | Greco | 568/772 |

FOREIGN PATENT DOCUMENTS

| | | | |
|---|---|---|---|
| 422098 | 11/1925 | Fed. Rep. of Germany | 564/446 |
| 2533920 | 2/1977 | Fed. Rep. of Germany | 568/772 |
| 53-101336 | 9/1978 | Japan | 564/446 |
| 56-68630 | 6/1981 | Japan | 568/772 |
| 56-83428 | 7/1981 | Japan | 568/772 |
| 57-142935 | 9/1982 | Japan | 568/772 |
| 60-139637 | 7/1985 | Japan | 568/772 |
| 63-130546 | 6/1988 | Japan | 568/772 |
| 63-222138 | 9/1988 | Japan | 568/772 |

OTHER PUBLICATIONS

ORGANIC SYNTHESIS, (1973), pp. 743-746, MEKLER et al., "2-Methyl-1,3-cyclohexanedione* (1,3-Cyclohexanedione, 2-methyl-)".

CHEM. zvesti 35 (1) 119-126 (1981), J. Sraga et al., "Methylation of 1,3-cyclopentanedione, 1,3-cyclohexanedione, and 1,3-cycloheptanedione with iodomethane in aprotic solvents in the absence and in the presence of 18-crown-6".

Primary Examiner—James H. Reamer
Attorney, Agent, or Firm—Stevens, Davis, Miller & Mosher

[57] ABSTRACT

A process for producing 2-methyl-1,3-cyclohexanedione which comprises subjecting 1,3-cyclohexanedione, formaldehyde and a dialkylamine to Mannich reaction to obtain a 2-dialkylaminomethyl-1,3-cyclohexanedione, and subjecting the 2-dialkylaminomethyl to hydrogenolysis, and a process for producing 2-methylresorcinol which comprises aromatizing 2-methyl-1,3-cyclohexanedione obtained. According to these processes, it is possible to produce high-purity 2-methylresorcinol and 2-methyl-1,3-cyclohexanedione commercially easily and advantageously.

15 Claims, No Drawings

PROCESS FOR PRODUCING 2-METHYL-1,3-CYCLOHEXANEDIONE AND 2-METHYLRESORCINOL

This invention relates to processes for producing 2-methylresorcinol and 2-methyl-1,3-cyclohexanedione.

2-Methylresorcinol is useful as an intermediate of various products such as pigments, dyes, hairdyes, synthetic resins, medicines, agricultural chemicals, photographic agents, etc and a lot of processes for producing 2-methylresorcinol have been proposed.

For example, Japanese Patent Application Kokai Nos. 56-68630, 56-83428, 57-142935, 60-139637, 63-130546 and 63-222138 describe processes for producing 2-methylresorcinol, which comprise tert-butylating resorcinol to obtain 4,6-di-tert-butylresorcinol, methylating 4,6-di-tert-butylresorcinol to obtain 2-methyl-4,6-di-tert-butylresorcinol and de-tert-butylating 2-methyl-4,6-di-tert-butylresorcinol.

Further, DE-OS 2533920 describes a process for producing 2-methylresorcinol which comprises aromatizing 2-methyl-1,3-cyclohexanedione prepared from 5-oxohexanoic acid ester.

2-Methyl-1,3-cyclohexanedione is, as described in DE-OS 2533920, useful as an intermediate of 2-methylresorcinol and is also useful as an intermediate of various products as 2-methylresorcinol is. As a process for producing 2-methyl-1,3-cyclohexanedione, besides the process described in DE-OS 2533920, there are known processes of methylating 1,3-cyclohexanedione by using methyl iodide, described in Org. Syn. Coll., 5, 743 (1973) and Chem. zvesti., 35, 119 (1981).

The process for producing 2-methylresorcinol by de-tert-butylating, described in Japanese Patent Application Kokai No. 56-68630, etc., has a lot of reaction steps and the de-tert-butylating requires a high temperature in the presence of a strong acid as well as recovering or treatment of isobutylene which is a by-product and therefore, the process is not commercially advantageous.

The process for producing 2-methylresorcinol by aromatizing 2-methyl-1,3-cyclohexanedione, described in DE-OS 2533920, requires a starting material which is not easily available.

Further, a process of methylating 1,3-cyclohexanedione which has been known as a process for producing 2-methyl-1,3-cyclohexanedione, is not commercially advantageous,, because methyl iodide used for introducing methyl groups is expensive and the yield of 2-methyl-1,3-cyclohexanedione is low.

Thus, as to 2-methylresorcinol and 2-methyl-1,3-cyclohexanedione which are useful as intermediates of various products, various processes for producing them have been proposed, but the processes are not commercially advantageous and therefore, a development of a commercially advantageous process for producing them has been strongly desired.

The present inventors have endeavored to develop a commercially easy and advantageous process for producing 2-methylresorcinol and 2-methyl-1,3-cyclohexanedione in high yields and as a result, they have found that when 1,3-cyclohexanedione is dialkylaminomethylated through Mannich reaction, a dialkylaminomethyl group reacts with 1,3-cyclohexanedione very selectively at the 2-position and the dialkylaminomethyl group introduced at the 2-position is easily converted to a methyl group through hydrogenolysis.

One of the objects of this invention is to provide a commercially easy and advantageous process for producing 2-methylresorcinol in high yields.

Another object of this invention is to provide a commercially easy and advantageous process for producing 2-methyl-1,3-cyclohexanedione in high yields.

A further object of this invention is to provide a novel 2-dialkylaminomethyl-1,3-cyclohexanedione and a process for producing the same.

Other objects and advantages of this invention will become apparent from the following description.

According to this invention, there are provided a process for producing 2-methyl-1,3-cyclohexanedione, which comprises reacting 1,3-cyclohexanedione, formaldehyde and a dialkylamine in an inert solvent and reacting the resulting 2-dialkylaminomethyl-1,3-cyclohexanedione with hydrogen, and a process for producing 2-methylresorcinol which comprises aromatizing said 2-methyl-1,3-cyclohexanedione.

The present reaction is represented by the following reaction scheme.

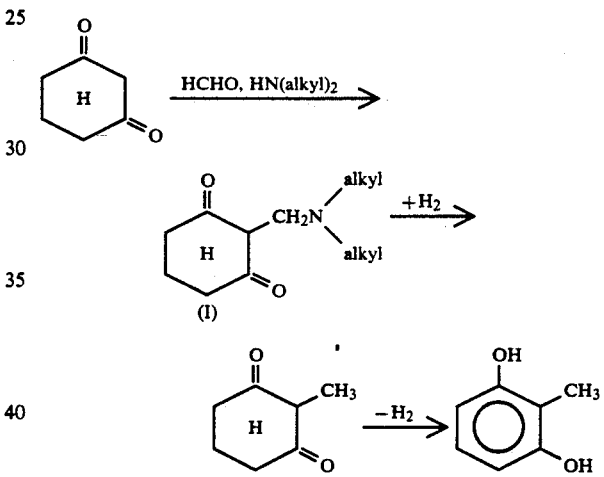

2-Dialkylaminomethyl-1,3-cyclohexanedione is a novel compound represented by formula (1).

The present process is described in detail below.

The reaction of 1,3-cyclohexanedione, formaldehyde and a dialkylamine can be carried out by a method known per se as Mannich reaction. As the dialkylamine, dimethylamine is most preferably used, and diethylamine, dipropylamine, piperidine or the like can be also used. The amount of the dialkylamine used is preferably 1-1.5 moles, more preferably 1.1-1.3 moles per mole of 1,3-cyclohexanedione.

The amount of formaldehyde used is preferably 1-1.5 moles, more preferably 1.1-1.3 moles per mole of 1,3-cyclohexanedione.

The inert solvent is at least one member selected from the group consisting of water and alcohols such as methanol, etc. and the amount of the inert solvent used is preferably 1-20 parts by weight, more preferably 3-5 parts by weight per part by weight of 1,3-cyclohexanedione.

The Mannich reaction is conducted under stirring, preferably in the range of a temperature of 10°-60° C.

2-Dialkylaminomethyl-1,3-cyclohexanedione thus obtained is preferably successively subjected to hydrogenolysis with hydrogen.

The hydrogenolysis can be conducted by introducing hydrogen gas in the liquid layer of 2-dialkylaminomethyl-1,3-cyclohexanedione at a temperature of 20°–200° C. under a pressure of normal pressure to 50 atmospheric pressure in the presence of a known hydrogenolysis catalyst such as palladium-carbon, Raney nickel, etc.

The amount of the hydrogenolysis catalyst used is not critical, but usually 0.1–20% by weight based on the weight of 2-dialkylaminomethyl-1,3-cyclohexanedione.

After completion of the hydrogenolysis, the reaction mixture may be directly subjected to aromatization through dehydrogenation, or the reaction mixture may be subjected to a conventional post-treatment to obtain crystals of 2-methyl-1,3-cyclohexanedione, post-treatment including, for example, adding water to the reaction mixture, if necessary, removing inert solvents such as alcohols by distillation and acidifying the residue whereby 2-methyl-1,3-cyclohexanedione is easily crystallized. The crystals can be isolated by filtration.

The aromatization of 2-methyl-1,3-cyclohexanedione through dehydrogenation can be conducted by a known method.

For example, it can be conducted by heating the liquid layer of 2-methyl-1,3-cyclohexanedione to 160°–250° C. in the presence of known dehydrogenation catalysts such as palladium-carbon, platinum-carbon, etc.

The heating can be conducted if necessary, under a nitrogen atmosphere.

The solvent for dehydrogenation includes, for example, alkylbenzenes such as mixed cymene, mesitylene, etc., polyalcohols such as dipropyleneglycol methyl ether, derivatives thereof and the like.

The amount of the solvent used is preferably 1–20 parts by weight per part by weight 2-methyl-1,3-cyclohexanedione. The amount of the catalyst used is not critical but preferably 0.5–20% by weight based on the weight of 2-methyl-1,3-cyclohexanedione.

After completion of the dehydrogenation, the catalyst while being hot is removed by filtration and the reaction mixture is cooled and the deposited crystal is isolated by filtration to obtain high-purity 2-methylresorcinol.

The dehydrogenation can be also conducted according to the process described in the specification of U.S. patent application Ser. No. 3,624,135, by using acetic anhydride and concentrated sulfuric acid and in this case, the product is subjected to hydrolysis to obtain the desired 2-methylresorcinol.

In the process of this invention, the first step of obtaining a 2-dialkylaminomethyl-1,3-cyclohexanedione, the second step of obtaining 2-methyl-1,3-cyclohexanedione through hydrogenolysis and the third step of obtaining 2-methylresorcinol through dehydrogenation are conducted successively, but the product of each step may be isolated or these steps may be successively conducted without isolation. Particularly, the first step and the second step can proceed successively with ease.

After the end of the first-step reaction has been confirmed, for example, by a high performance liquid chromatography, the prescribed hydrogenolysis catalyst is added to the reaction mixture of the first step and hydrogen gas is introduced thereto, whereby the second step product is obtained. The excessive formaldehyde and/or dialkylamine of the first step, even if it exists in the reaction system, does not adversely affect the hydrogenolysis reaction. After the end of the second-step reaction has been confirmed, the third step can be conducted successively. In the third step, the prescribed dehydrogenation catalysts and the prescribed solvent are added to the reaction mixture of the second step; the resulting mixture is heated; a solvent having comparatively low boiling point is removed by distillation and the residue is heated at the prescribed temperature, whereby dehydrogenation can be completed. When a catalyst for both hydrogenolysis and dehydrogenation, such as palladium-carbon is used, it is not necessary to add a further catalyst in the third step.

According to the process of the present invention, it is possible to produce high-purity 2-methylresorcinol and 2-methyl-1,3-cyclohexanedione, commercially easily and advantageously.

The present invention is described below in fuller detail in the Examples. However, the present invention is not limited thereto. In the Examples, parts and % are by weight unless otherwise specified.

EXAMPLE 1

In a reactor equipped with a stirrer, 300 parts of methanol, 56 parts of 50% aqueous solution of dimethylamine and 56 parts of 1,3-cyclohexanedione were placed and the temperature of the mixture was raised to 30° C. Thereafter, 53 parts of 37% aqueous solution of formaldehyde was added dropwise for an hour. After adding, the reaction solution was maintained at 40° C. for 3 hours. The end of the reaction was confirmed by checking the amount of the remaining unreacted material (1,3-cyclohexanedione) by a high performance liquid chromatography.

Then, 10 parts of 5% palladium-carbon was added to the resulting reaction mixture and hydrogen was blown over 15 hours at 30° C. under normal pressure. The end of the reaction was confirmed by checking the amount of the remaining unreacted material (2-dimethylaminomethyl-1,3-cyclohexanedione).

After completion of the reaction, the catalyst was removed by filtration at 30° C. and 300 parts of water was added to the reaction mixture and methanol was removed by distillation, after which the residue was adjusted to pH 6 by adding 35% hydrochloric acid. The resulting precipitate was separated by filtration, washed with water, and was dried at 70° C. to obtain 54.8 parts of a dry cake of 2-methyl-1,3-cyclohexanedione (yield: 87.0%).

The composition analysis of the dry cake by a high performance liquid chromatography revealed that the purity of 2-methyl-1,3-cyclohexanedione was 97.2%.

The melting point of the dry cake was 206°–208° C. (the value described in literature: 207°–209° C.). The FD-mass spectrum of the dry cake had a peak at 126 and the value was the same as the theoretical molecular weight.

EXAMPLE 2

The procedure of Example 1 was repeated except that as the solvent for Mannich reaction and hydrogenolysis, water was used in place of methanol and therefore no removal of methanol by distillation was necessitated and hydrogenolysis was conducted at 60° C. under normal pressure for 20 hours, to obtain 56.3 parts of a dry cake of 2-methyl-1,3-cyclohexanedione (yield: 89.4%).

The composition analysis of the dry cake by a high performance liquid chromatography revealed that the purity of 2-methyl-1,3-cyclohexanedione was 96.9%.

EXAMPLE 3

In a reactor equipped with a stirrer, 50 parts of 2-methyl-1,3-cyclohexanedione obtained in Example 1, parts of mesitylene and 15 parts of 5% palladium-carbon were placed and the mixture was maintained at 160°-165° C. for 10 hours with dehydrating under a nitrogen atmosphere.

The end of the reaction was confirmed by checking the amount of the remaining unreacted material (2-methyl-1,3-cyclohexanedione) by a high performance liquid chromatography.

The catalyst was removed by filtration at 120° C. and the filtrate was cooled to 5° C. The resulting precipitate was separated by filtration, washed with n-hexane and dried at 70° C. to obtain 34.9 parts of a dry cake of 2-methylresorcinol (yield: 71.0%).

The composition analysis of the dry cake by a high performance liquid chromatography revealed that the purity of 2-methyl-1,3-cyclohexanedione was 98.2%. The melting point of the dry cake was 119.0°-120.5° C.

The quantitative analysis of the filtrate showed the unreacted material (23 mole % of 2-methyl-1,3-cyclohexanedione) and 5 mole % of 2-methylresorcinol.

EXAMPLE 4

2-Methyl-1,3-cyclohexanedione obtained in Example 2 was aromatized through dehydrogenation in the same procedure as in Example 3, to obtain 34.4 parts of 2-methylresorcinol (yield: 69.9%).

The composition analysis by a high performance liquid chromatography revealed that the purity of 2-methylresorcinol was 98.2%.

The quantitative analysis of the filtrate showed the unreacted material (22 mole % of 2-methyl-1,3-cyclohexanedione) and 5 mole % of 2-methylresorcinol.

EXAMPLE 5

The Mannich reaction and hydrogenolysis were conducted in the same procedure as in Example 1. To the reaction mixture was added 500 parts of mesitylene and methanol was removed by distillation under a nitrogen atmosphere, after which the residue was maintained at 160°-165° C. for 10 hours.

After completion of the aromatization, the product was separated in the same procedure as in Example 3, to obtain 39.1 parts of a dry cake of 2-methylresorcinol (yield: 63.1%).

The composition analysis by a high performance liquid chromatography revealed that the purity of 2-methylresorcinol was 98.0%.

The quantitative analysis of the filtrate showed 3 mole % of resorcinol, 21 mole % of 2-methyl-1,3-cyclohexanedione and 5 mole % of 2-methylresorcinol.

What is claimed is:

1. A process for producing 2-methyl-1,3-cyclohexanedione which comprises reacting 1,3-cyclohexanedione, formaldehyde and a dialkylamine or piperidine in an inert solvent and reacting the resulting 2-dialkylaminomethyl-1,3-cyclohexanedione with hydrogen in the presence of a hydrogenolysis catalyst.

2. The process according to claim 1, wherein the dialkylamine is dimethylamine, diethylamine or dipropylamine.

3. The process according to claim 1, wherein the dialkylamine is dimethylamine.

4. The process according to claim 1, wherein the dialkylamine or piperidine is used in an amount of 1-1.5 moles per mole of 1,3-cyclohexanedione.

5. The process according to claim 1, wherein the dialkylamine or piperidine is used in an amount of 1.1-1.3 moles per mole of 1,3-cyclohexanedione.

6. The process according to claim 1, wherein the formaldehyde is used in an amount of 1-1.5 moles per mole of 1,3-cyclohexanedione.

7. The process according to claim 1, wherein the formaldehyde is used in an amount of 1.1-1.3 moles per mole of 1,3-cyclohexanedione.

8. The process according to claim 1, wherein the inert solvent is at least one member selected from the group consisting of water and alcohols 9. The process according to claim 1, wherein the amount of inert solvent is 1-20 parts by weight per part by weight of 1,3-cyclohexanedione.

10. The process according to claim 1, wherein the amount of inert solvent is 3-5 parts by weight per part by weight of 1,3-cyclohexanedione.

11. The process according to claim 1, wherein the reaction of 1,3-cyclohexanedione, formaldehyde and a dialkylamine is effected at a temperature of 10°-60° C.

12. The process according to claim 1, wherein the reaction of 2-dialkylaminomethyl-1,3-cyclohexanedione and hydrogen is effected at a temperature of 20°-200° C. under a pressure of normal pressure to 50 atmospheric pressure.

13. The process according to claim 1, wherein the hydrogenolysis catalyst is palladium-carbon or Raney nickel.

14. The process according to claim 1, wherein the hydrogenolysis catalyst is used in an amount of 0.1-20% by weight based on the weight of 1,3-cyclohexanedione.

15. A process for producing 2-dialkylaminomethyl-1,3-cyclohexanedione which comprises reacting 1,3-cyclohexanedione, formaldehyde and a dialkylamine or piperidine in an inert solvent.

* * * * *

UNITED STATES PATENT AND TRADEMARK OFFICE
CERTIFICATE OF CORRECTION

PATENT NO. : 5,276,198
DATED : January 4, 1994
INVENTOR(S) : Toshio NAKAMATSU, Yasuhiro NISHIDA and Norio KOMETANI It is certified that error appears in the above-indentified patent and that said Letters Patent is hereby corrected as shown below:

At column 5, line 22, "2-methyl-1,3-cyclohexanedione" should read --2-methylresorcinol--.

Signed and Sealed this

Twenty-second Day of August, 1995

Attest:

BRUCE LEHMAN

*Attesting Officer*  *Commissioner of Patents and Trademarks*